(12) United States Patent
Saebo

(10) Patent No.: US 11,914,653 B1
(45) Date of Patent: Feb. 27, 2024

(54) SYSTEMS AND METHODS FOR REMOVING HUMAN GENETIC DATA FROM GENETIC SEQUENCES

(71) Applicant: Pathogenomix, Inc., Santa Cruz, CA (US)

(72) Inventor: Oystein Friestad Saebo, Santa Cruz, CA (US)

(73) Assignee: Pathogenomix, Inc., Santa Cruz, CA (US)

( * ) Notice: Subject to any disclaimer, the term of this patent is extended or adjusted under 35 U.S.C. 154(b) by 0 days.

(21) Appl. No.: 18/100,074

(22) Filed: Jan. 23, 2023

(51) Int. Cl.
| | |
|---|---|
| *G06F 16/906* | (2019.01) |
| *G06F 16/901* | (2019.01) |
| *G06F 16/903* | (2019.01) |
| *G16B 30/00* | (2019.01) |
| *G16B 40/00* | (2019.01) |
| *G16B 50/30* | (2019.01) |

(52) U.S. Cl.
CPC ........ *G06F 16/906* (2019.01); *G06F 16/9014* (2019.01); *G06F 16/90344* (2019.01); *G16B 30/00* (2019.02); *G16B 40/00* (2019.02); *G16B 50/30* (2019.02)

(58) Field of Classification Search
None
See application file for complete search history.

(56) References Cited

PUBLICATIONS

Decouchant, Jérémie, et al. "Accurate filtering of privacy-sensitive information in raw genomic data." Journal of biomedical informatics 82 (2018): 1-12.*

* cited by examiner

*Primary Examiner* — G. Steven Vanni
(74) *Attorney, Agent, or Firm* — Foley & Lardner LLP

(57) ABSTRACT

Systems and methods for removing data from strings are disclosed. A system can access a first hash table that stores representations of a first set of strings, where the representations have predetermined number of characters. The system can generate a second hash table that stores a second representations of a string of a second set of strings, where the second representations have the predetermined number of characters. Upon determining that the first hash table includes at least one of the plurality of second representations of the string included in the second hash table, the system can increment a counter associated with the string. The system can generate a third set of strings by removing the string from the second set of strings responsive to determining that the counter satisfies a threshold, and transmit the third set of strings to a computing system.

20 Claims, 5 Drawing Sheets

SYSTEMS AND METHODS FOR REMOVING HUMAN GENETIC DATA FROM GENETIC SEQUENCES

BACKGROUND

String data processing can be utilized to identify information present in strings. Although string matching can be utilized to detect the presence of information in strings, such processing techniques are impracticable to perform when attempting to match smaller string segments present in increasingly large datasets.

SUMMARY

The systems and methods described herein enable for fast and secure transmission of information by efficiently removing private, sensitive, or secure data from strings prior to data transmission. Certain strings may include information that cannot be transmitted outside of a local computer network environment. The systems and methods described herein can automatically detect information for which transmission is not permitted, and automatically remove that information from a data package that is ultimately transmitted outside of a local computer network environment. Existing computer-based technology is only capable of utilizing brute-force scanning and comparisons to determine whether information matches to other information. However, as the information to be transmitted or matched increases in size, the number of comparisons that must be performed increases exponentially, making brute-force approaches impracticable.

To address these issues, the systems and methods described herein can automatically determine whether information to be transmitted matches to an existing corpus of information via efficient hash tables, and by iteratively processing segments of the information (e.g., as strings). In doing so, the systems and methods described herein can efficiently identify and remove any information that matches to the protected corpus, thereby improving both network security and reducing the amount of computational resources required to protect secure data from being transmitted outside of a local network. These and other improvements are described in further detail herein.

At least one aspect of the present disclosure is directed to a system. The system can include one or more processors coupled to memory. The system can access a hash table that stores a plurality of first k-mers of a human genome. Each first k-mer of the plurality of first k-mers can correspond to a predetermined number of characters (k). The system can generate a plurality of second k-mers of a read of a cluster of a plurality of clusters, the plurality of clusters obtained from a sample. The system can determine a number of the plurality of second k-mers that match at least one of the plurality of first k-mers in the hash table. The system can generate a subset of the plurality of clusters by removing the cluster from the plurality of clusters responsive to the number satisfying a threshold. The system can transmit the subset of the plurality of clusters to a computing system.

In some implementations, the system can generate the hash table that stores the plurality of first k-mers of the human genome. Each of the plurality of first k-mers can correspond to non-overlapping portions of the human genome. In some implementations, the system can generate the plurality of second k-mers based on each base in the read. In some implementations, the system can generate a second hash table based on the plurality of second k-mers.

In some implementations, the system can determine the number based on the hash table and the second hash table.

In some implementations, each of the plurality of first k-mers have a length of one of at least fifteen, at least thirty, at least forty-five, or at least fifty. In some implementations, the system can determine the number by performing a lookup in the hash table using each of the plurality of second k-mers. In some implementations, the system can store an association between the cluster and an identifier of a chromosome to which the plurality of first k-mers correspond. In some implementations, the system can extract the plurality of first k-mers from one or more of a FASTA format file, a FASTQ format file, a FASTQ.GZ format file, an FNA format file, or a BAM format file of the human genome. In some implementations, the plurality of first k-mers correspond to a first chromosome file of the human genome.

At least one other aspect of the present disclosure is directed to another system. The system can include one or more processors coupled to memory. The system can access a first hash table that stores a plurality of first k-mers of a human genome. Each k-mer of the plurality of first k-mers can correspond to a predetermined number of characters (k). The system can generate a second hash table that stores a plurality of second k-mers of a read of a cluster of plurality of clusters obtained from a sample of a pathogen. Each second k-mer of the plurality of second k-mers can correspond to the predetermined number of characters (k). Responsive to determining, based on the first hash table and the second hash table, that the first hash table includes at least one of the plurality of second k-mers of the read included in the second hash table, the system can increment a counter associated with the cluster. The system can generate a subset of the plurality of clusters by removing the cluster from the plurality of clusters responsive to determining that the counter satisfies a threshold. The system can transmit the subset of the plurality of clusters to a computing system.

In some implementations, the system can generate the first hash table that stores the plurality of first k-mers of the human genome. In some implementations, each of the plurality of first k-mers can correspond to non-overlapping portions of the human genome. In some implementations, the system can generate the plurality of second k-mers based on each base in the read. In some implementations, the system can present an indication of a chromosome in the human genome to which the cluster corresponds.

Yet another aspect of the present disclosure is directed to yet another system. The system can include one or more processors coupled to memory. The system can generate a hash table that stores a plurality of representations of a first set of strings. Each representation of the plurality of representations can corresponding to a predetermined number of characters. The system can, for each string in a second set of strings, generate a string segment of the string having the predetermined number of characters; and responsive to determining that the string segment corresponds to at least one of the plurality of representations of the first set of strings in the hash table, increment a counter associated with the second set of strings. The system can remove the string from a plurality of strings responsive to the counter satisfying a threshold.

In some implementations, the first set of strings corresponds to genetic data of a human genome. In some implementations, the string segment comprises a k-mer. In some implementations, the system can determine that the string segment corresponds to at least one of the plurality of representations in the hash table by performing a lookup in the hash table using the k-mer.

Yet one other aspect of the present disclosure is directed to another system. The system can include one or more processors coupled to memory. The system can access a first hash table that stores a plurality of representations of a first set of strings. Each representation of the plurality of representations can correspond to a predetermined number of characters. The system can generate a second hash table that stores a plurality of second representations of a string of a second set of strings. Each second representation of the plurality of second representations can correspond to the predetermined number of characters. Responsive to determining, based on the first hash table and the second hash table, that the first hash table includes at least one of the plurality of second representations of the string included in the second hash table, the system can increment a counter associated with the second set of strings. The system can generate a third set of strings by removing the string from the second set of strings responsive to determining that the counter satisfies a threshold. The system can transmit the third set of strings to a computing system.

In some implementations, the system can pre-process a sequence file to generate the first set of strings. In some implementations, the second hash table corresponds to a cluster of genetic information obtained from a sample.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the present disclosure can be combined with other aspects. Aspects can be implemented in any convenient form. For example, by appropriate computer programs, which may be carried on appropriate carrier media (computer readable media), which may be tangible carrier media (e.g. disks) or intangible carrier media (e.g. communications signals). Aspects may also be implemented using suitable apparatus, which may take the form of programmable computers running computer programs arranged to implement the aspect. As used in the specification and in the claims, the singular form of "a," "an," and "the" include plural referents unless the context clearly dictates otherwise.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

Figure 1:
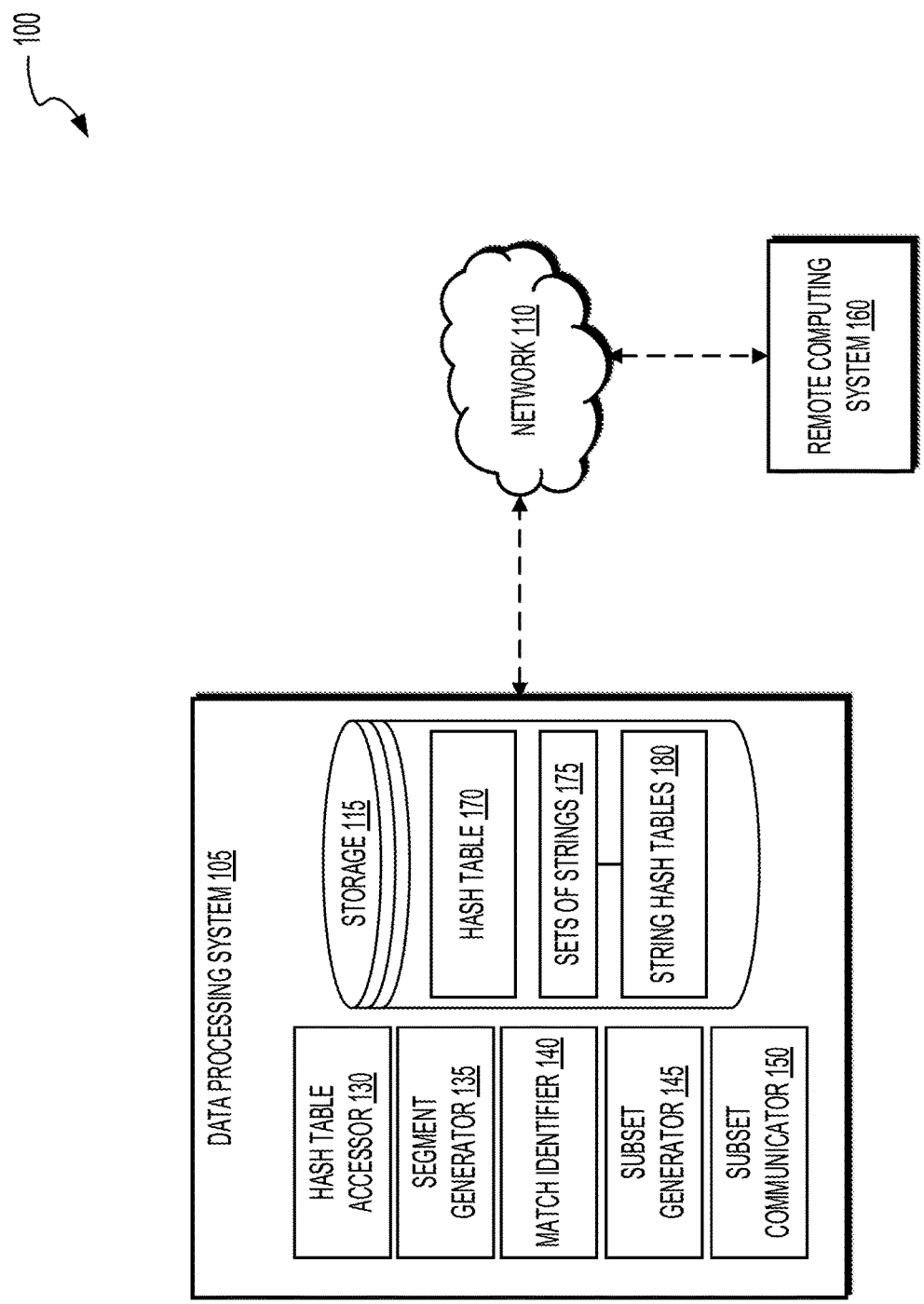
FIG. 1 illustrates an example system for removing data from strings, in accordance with one or more implementations.

Below are detailed descriptions of various concepts related to and implementations of techniques, approaches, methods, apparatuses, and systems for removing data from strings. The various concepts introduced above and discussed in detail below may be implemented in any of numerous ways, as the described concepts are not limited to any particular manner of implementation. Examples of specific implementations and applications are provided primarily for illustrative purposes.

Certain strings may include information that cannot be transmitted outside of a local computer network environment. The systems and methods described herein can automatically detect information for which transmission is not permitted, and automatically remove that information from a data package that is ultimately transmitted outside of a local computer network environment. This both improves network security and reduces the overall consumption of network resources by the local computer network.

Existing computer-based technology is only capable of utilizing brute-force scanning and comparisons to determine whether information matches to other information. However, as the information to be transmitted or the corpus of protected information increases in size, the number of comparisons that must be performed increases exponentially, making brute-force approaches impracticable. To address these and other issues, the systems and methods described herein can automatically determine whether information to be transmitted matches to an existing corpus of protected information via efficient hash tables, and by iteratively processing segments of the information (e.g., as strings). In doing so, the techniques described herein can be used to efficiently identify and remove any information that matches to the protected corpus, thereby improving both network security and reducing the amount of computational resources required to protect secure data from being transmitted outside of a local network.

One example use case for the present techniques includes the automatic removal of sequence data from samples that happens to match that of the human genome. In various embodiments, deoxyribonucleic acid (DNA) sequence data from pathogenic samples may be transmitted from a hospital or healthcare provider network to an external computing system. However, though rare, randomness in sequence files intended to contain only information from pathogens' own genomes may coincide or include sequence data from a human genome.

Sometimes, it can be the case that a section of the human genome can match a section of a pathogen genome for a few hundred base pairs. Human genome data itself can be considered private or protected information that cannot be transmitted to external systems. Transmitting a coincidentally matching section of pathogen and human genome can constitute the transmission of protected data, thereby introducing a security risk.

The techniques described herein can be utilized to automatically detect and avoid accidental transmission of such information by discovering and removing any reads which match any part of the human genome before transmission. To do so, the systems and methods described herein can generate k-mers from source human genome data, and remove any reads, operational taxonomic units (OTUs), or clusters that include k-mers that match the human genome k-mers. Rather than implementing existing brute-force techniques, the techniques described herein generate and access efficient hash tables that improve processing efficiency. Automatically removing protected information from transmissions to external systems improves the overall security of local computer networks. These and other improvements are detailed herein.

Referring to FIG. 1, illustrated is a block diagram of an example system 100 for removing data from strings, in accordance with one or more implementations. The system 100 can include at least one data processing system 105, at least one network 110, and at least one remote computing system 160. The data processing system 105 can include a hash table accessor 130, a segment generator 135, a match identifier 140, a subset generator 145, a subset communicator 150, and storage 115. The storage 115 can include one or more hash tables 170, one or more sets of strings 175, and string hash tables 180. Although shown here as internal to the data processing system 105, the storage 115 can be external to the data processing system 105, for example, as a part of a local storage repository.

Each of the components (e.g., the data processing system 105, the network 110, the remote computing system 160, the hash table accessor 130, the segment generator 135, the match identifier 140, the subset generator 145, the subset communicator 150, the storage 115, etc.) of the system 100 can be implemented using the hardware components or a combination of software with the hardware components of a computing system, such as the computing system 500 described in connection with FIG. 5, or any other computing system described herein. Each of the components of the data processing system 105 can perform the functionalities detailed herein.

The data processing system 105 can include at least one processor and a memory (e.g., a processing circuit). The memory can store processor-executable instructions that, when executed by a processor, cause the processor to perform one or more of the operations described herein. The processor may include a microprocessor, an application-specific integrated circuit (ASIC), a field-programmable gate array (FPGA), a graphics processing unit (GPU), etc., or combinations thereof. The memory (which may be or include the storage 115) may include, but is not limited to, electronic, optical, magnetic, or any other storage or transmission device capable of providing the processor with program instructions. The memory may further include a floppy disk, CD-ROM, DVD, magnetic disk, memory chip, ASIC, FPGA, read-only memory (ROM), random-access memory (RAM), electrically erasable programmable ROM (EEPROM), erasable programmable ROM (EPROM), flash memory, optical media, or any other suitable memory from which the processor can read instructions. The instructions may include code from any suitable computer programming language. The data processing system 105 can include one or more computing devices or servers that can perform various functions as described herein. The data processing system 105 can include any or all of the components and perform any or all of the functions of the computer system 500 described in connection with FIG. 5.

In some implementations, the data processing system 105 may communicate with the remote computing system 160, for example, to provide information stored in strings (e.g., sequence reads corresponding to a pathogenic sample). In one example, the data processing system 105 can be or can include an application server or webserver, which may include software modules to access or transmit data stored by the data processing system 105 (e.g., in the storage 115). For example, the data processing system 105 may include a webserver allowing the remote computing system 160 to request one or more strings, sequence reads, or other genetic data corresponding to one or more samples. In response, the data processing system 105 can perform the techniques described herein to remove any protected information from the requested data and transmit the secure information to the remote computing system 160. In some implementations, the data processing system 105 can transmit data to the remote computing system 160 in response to user input by an operator of the data processing system 105.

The network 110 can include computer networks such as the Internet, local, wide, or other area networks, intranets, and satellite networks, other computer networks such as voice or data mobile phone communication networks, or combinations thereof. The data processing system 105 of the system 100 can communicate via the network 110 with one or more computing devices, such as the remote computing system 160. The network 110 may be any form of computer network that can relay information between the data processing system 105 and the remote computing system 160. In some implementations, the network 110 may include the Internet and/or other types of data networks, such as a local area network (LAN), a wide area network (WAN), a cellular network, a satellite network, or other types of data networks. The network 110 may also include any number of computing devices (e.g., computers, servers, routers, network switches, etc.) that are configured to receive or transmit data within the network 110.

The network 110 may further include any number of hardwired or wireless connections. Any or all of the computing devices described herein (e.g., the data processing system 105, the remote computing system 160, the computer system 500, etc.) may communicate wirelessly (e.g., via Wi-Fi, cellular communication, radio, etc.) with a transceiver that is hardwired (e.g., via a fiber optic cable, a CAT5 cable, etc.) to other computing devices in the network 110. Any or all of the computing devices described herein (e.g., the data processing system 105, the remote computing system 160, the computer system 500, etc.) may also communicate wirelessly with the computing devices of the network 110 via a proxy device (e.g., a router, network switch, or gateway).

The remote computing system 160 can include at least one processor and a memory (e.g., a processing circuit). The memory can store processor-executable instructions that, when executed by the processor, cause the processor to perform one or more of the operations described herein. The processor can include a microprocessor, an ASIC, an FPGA, a GPU, etc., or combinations thereof. The memory can include, but is not limited to, electronic, optical, magnetic, or any other storage or transmission device capable of providing the processor with program instructions. The memory can further include a floppy disk, CD-ROM, DVD, magnetic disk, memory chip, ASIC, FPGA, ROM, RAM, EEPROM, EPROM, flash memory, optical media, or any other suitable memory from which the processor can read instructions. The instructions can include code from any suitable computer programming language. The remote computing system 160 can include one or more computing devices, servers, personal computing devices, or data repositories. The remote computing system 160 can include any or all of the components and perform any or all of the functions of the computer system 500 described in connection with FIG. 5.

The storage 115 can be a computer-readable memory that can store or maintain any of the information described herein. The storage 115 can store or maintain one or more data structures, which may contain, index, or otherwise store each of the values, pluralities, sets, variables, vectors, numbers, or thresholds described herein. The storage 115 can be accessed using one or more memory addresses, index values, or identifiers of any item, structure, or region maintained in the storage 115. In implementations where the storage 115 is external to the data processing system 105, the storage 115 can be accessed by the components of the data processing system 105 via the network 110 or via a local communications interface. The storage 115 can be distributed across many different computer systems or storage elements. The data processing system 105 can store, in one or more regions of the memory of the data processing system 105, or in the storage 115, the results of any or all computations, determinations, selections, identifications, generations, constructions, or calculations in one or more data structures indexed or identified with appropriate values.

Any or all values stored in the storage 115 may be accessed by the components of the data processing system 105 to perform any of the functionalities or functions described herein. In some implementations, the data processing system 105 may utilize authentication information (e.g., username, password, email, etc.) to show that an operator of the data processing system 105 is authorized to access requested information in the storage 115. The storage 115 may include permission settings that indicate which users, devices, or profiles are authorized to access certain information stored in the storage 115.

The storage can store one or more hash tables 170, for example, in one or more data structures or files. The hash table 170 can be generated from a corpus of protected information that is not authorized for transmission to the remote computing system 160 via the network 110. The protected corpus of information may be, for example, the human genome. Utilizing the hash table 170 to store representations of the protected corpus improves the overall computational efficiency of the techniques described herein. The hash table 170 can be generated and populated using k-mers extracted from human genome data, as described herein.

The k-mers described herein can be substrings of a predetermined length (k) that are extracted from a biological sequence. When representing DNA, k-mers are composed of nucleotides (e.g., A, T, G, and C). K-mers can be utilized to represent portions of DNA sequences, improve heterologous gene expression, identify species in metagenomic samples, and create attenuated vaccines. The term k-mer can refer to all of a sequence's subsequences of length k. For example, the sequence AGAT would have four monomers (A, G, A, and T), three 2-mers (AG, GA, AT), two 3-mers (AGA and GAT) and one 4-mer (AGAT). Generally, a sequence of length L will have L−k+1 k-mers and $n^k$ total possible k-mers, where n is number of possible monomers (e.g. four in the case of DNA).

The k-mers extracted from the human genome data can have a predetermined length (e.g., fifteen base pairs, thirty base pairs, etc.). The predetermined length may be configurable when the hash table 170 is generated. In some embodiments, multiple hash tables 170 that each correspond to different k-mer lengths may be stored in the storage 115. Generating the hash table 170 can include pre-processing the information in the protected corpus (e.g., removing filler "N" bases, removing header information, etc.). In implementations where the hash table 170 corresponds to a human genome, multiple respective hash tables 170 can be generated and stored for each chromosome in the human genome. In some implementations, a hash table 170 includes representations of unique non-overlapping k-mers of a predetermined length extracted from a corresponding chromosome of the human genome. Techniques for generating the hash tables 170 are described in further detail herein.

The storage can store one or more sets of strings 175, for example, in one or more data structures or files. Each set of strings may be information that potentially includes protected data represented in part by the hash table(s) 170. For example, the set of strings 175 can correspond to a pathogenic sample, and a string in the set of strings can correspond to a cluster of genetic information (e.g., base pairs) of the pathogenic sample. A string corresponding to a cluster may include genetic information that coincides with portions of the human genome represented by a hash table 170. Using the techniques described herein, the components of the data processing system 105 can detect which strings (and therefore clusters) include information represented in the hash table 170 (and therefore a chromosome of the human genome), and remove the string from the corresponding set of strings 175 prior to transmission. Each string in a set of strings 175 may include any number of base pairs from a cluster of genetic material. A cluster can be a genetic building block of a pathogen (e.g., a virus, bacteria, or archaea). The storage 115 may store multiple sets of strings 175 that each correspond to a respective pathogen. Each string in a set of strings 175 can be utilized to generate one or more string hash tables 180, as described herein.

The storage can store one or more string hash tables 180, for example, in one or more data structures or files. Each string hash table 180 can be generated from a corresponding string of a set of strings 175. As described herein, string of a set of strings 175 can include genetic information from a cluster of a pathogenic sample. The string, which corresponds to a respective cluster, can include a number of sequential base pairs. The string hash table 180 corresponding to a cluster (e.g., generated from a corresponding string of the set of strings) can include overlapping k-mers (of a predetermined length, e.g., the predetermined length used when generating the hash table 170) extracted from the cluster. For example, the string hash table 180 can be generated by iterating through a read (e.g., the most abundant read) in a cluster base-by-base, and generating all possible k-mers while shifting one base at a time, such that the generated k-mers overlap by the predetermined length (k) minus one. The string hash table 180 can be generated for each string in each set of strings 175 (e.g., each cluster for each pathogenic sample). The string hash table 180 can be utilized by the components of the data processing system 105 to determine which strings (e.g., clusters) include genetic information corresponding to the human genome.

Referring now to the operations of the components of the data processing system 105, the hash table accessor 130 can access one or more hash tables 170 that store representations of a first set of strings. The first set of strings can be, for example, reads from a human genome. As described herein, each hash table 170 can correspond to a respective chromosome of the human genome. The hash table 170 can represent each unique k-mer of a predetermined length (k) that appears in the respective chromosome. The hash table accessor 130 can access each hash table 170 iteratively, for example, to match the contents of the hash table 170 to corresponding k-mers generated from one or more reads of a pathogenic sample, as described herein. For example, the hash table accessor 130 can be utilized to access a hash table 170 for a respective chromosome per iteration, until all hash tables 170 have been accessed and matched to the k-mers of the sample.

In some implementations, the hash table accessor 130 can generate the hash table(s) 170 corresponding to the human genome, for example, in a processing step that occurs prior to pathogenic sample matching. To do so, the hash table accessor 130 can extract k-mers from a file that includes base pairs of one or more chromosomes of the human genome. The file can be any suitable file, including a FASTA format file, a FASTQ format file, a FASTQ.GZ format file, an FNA format file, or a BAM format file, among others. When accessing the file corresponding to the human genome, the hash table accessor 130 can parse header information of the file to identify regions of the file that correspond to chromosome data (e.g., identify a "PRIMARY ASSEMBLY" header for each chromosome, etc.). To generate a hash table 170 for a chromosome, the hash table accessor 130 can first remove any "N" bases from the chromosome base pair data, which may indicate filler data.

The hash table accessor 130 can append the bases to a temporary string for the respective chromosome, base by base. When the temporary string is longer than a predetermined length (e.g., the predetermined k-mer size k, etc.), the hash table accessor 130 can remove the bases for that k-mer and write the removed k-mer to a new file (e.g., FASTA, FASTAQ, FNA, BAM, etc.) and add the removed k-mer to a hash table 170. The files used to represent the genetic information as described herein can be formed in a text-based format (or a text-based format compressed using a suitable compression algorithm) for representing nucleotide sequences or amino acid (e.g., protein) sequences, in which nucleotides or amino acids are represented using single-letter codes. In a FASTA file format, sequence names and comments can precede the sequences.

If a hash table 170 does not exist for the particular chromosome, the hash table accessor 130 can generate an empty hash table 170 for the chromosome (e.g., store in the storage 115 in association with a respective chromosome identifier, etc.). The hash table 170 may be referred to as a "hash map" or a "dictionary." The hash table 170 can be a data structure that implements a set abstract data type, which provides a structure that can map keys to values (e.g., k-mers). The hash table 170 can utilize a hash function to compute an index (which may be referred to as a "hash code") into an array of buckets or slots defined in the hash table 170 data structure, from which the desired value can be found. During lookup, the key is hashed and the resulting hash indicates where the corresponding value is stored. The hash function for the hash table 170 can assign each key to a unique bucket (e.g., a perfect hash function). In some embodiments, an imperfect hash function may be utilized with a technique to accommodate hash collisions, should they arise.

The hash table accessor 130 can parse the human genome file (e.g., which may be provided by or retrieved from another computing system) to generate a respective hash table 170 for each chromosome in the human genome. As described herein, the hash table accessor 130 can utilize a predetermined k-mer length (k) when generating the hash tables 170, which may be provided via user input or retrieved from a local configuration file. The predetermined length may be, for example, fifteen characters, thirty characters, or another suitable length. Once generated, the hash tables 170 can be stored in the storage 115 in association with a respective identifier of the chromosome to which they correspond along with an identifier of the predetermined length k. The hash tables 170 can include only unique k-mers for their corresponding chromosome. The generated hash tables 170 can be utilized by the hash table accessor 130 or the other components of the data processing system 105 to perform the various functionalities described herein.

The segment generator 135 can generate one or more string hash tables 180 that store second representations of a string of a second set of strings. As described herein, the string can include genetic information from a cluster of a genetic sample of a pathogen. A cluster can be a genetic building block that makes up the genome of the pathogen, and can include a series of sequential base pairs. Using techniques similar to those described in connection with the hash tables 170, the segment generator 135 can generate respective empty string hash tables 180 for each cluster. The clusters may be generated, for example, by a pre-processor executed by the data processing system 105 over genetic information from a sample of genetic data from a pathogen, or provided or retrieved from another computing system. A cluster, for example, can correspond to a string in a set of strings 175. In an embodiment, the string can correspond to a most abundant read in a cluster.

For each string in a set of strings that is not indicated as corresponding to the human genome, the segment generator 135 can iterate through the string base-by-base, shifting one base at a time, to generate overlapping k-mers. The k-mers can be extracted, for example, by iteratively extracting characters from the string using a "sliding window" having a number of characters equal to the predetermined length k, with a stride of one character (e.g., one base). In some implementations, the stride may be greater than one base (e.g., two bases, three bases, any range of bases up to and including the predetermined length, greater than the predetermined length, etc.). The overlapping k-mers can overlap by the k-mer size minus one base. Upon generation, the segment generator 135 can add the extracted k-mer to the string hash table 180 corresponding to the respective string. Each string hash table 180 generated respectively for each string of a set of strings 175 of a genetic sample of a pathogen can be utilized to determine which clusters (e.g., strings) to remove from the sample prior to transmission.

The match identifier 140 can determine that the first hash table includes at least one of the plurality of second representations (e.g., k-mer, hash of the k-mer, etc.) of the string (e.g., the cluster included in a corresponding string hash table 180. One approach to doing so involves scanning through each hash table 170 (e.g., each file corresponding to a chromosome) to determine if any k-mers in the hash table 170 match to a respective k-mer in the string hash tables 180 (e.g., corresponding to clusters of a sample). As part of an iterative process, the match identifier 140 can loop through each hash table 170 (e.g., each chromosome of the human genome) by iteratively selecting one hash table 170. In an iteration, the match identifier 140 can select one of a hash table 170 to match to the string hash tables 180 for a sample. The match identifier 140 can iterate through each string segment (e.g., k-mer) in the selected hash table 170, and determine whether the respective string segment is present in any of the string hash tables 180 (e.g., corresponding to a pathogenic sample). For example, the match identifier 140 can iteratively select each string hash table 180, each of which correspond to a respective string (e.g., a respective cluster of a genetic sample of a pathogen), and determine whether any of the string segments (e.g., k-mers) in the selected hash table 170 are present in the selected string hash table 180.

If the match identifier 140 determines that a string segment in the selected hash table 170 is present in the selected string hash table 180 (e.g., by performing a lookup, etc.), the match identifier 140 can increment a counter corresponding to the string (e.g., cluster) to which the string hash table 180 corresponds. The counter can indicate, for example, the number of matching k-mers in the cluster that are present in the human genome. The match identifier 140 can repeat this process for each string hash table 180 associated with a set of strings 175 (e.g., for a particular genetic sample), and for each hash table 170, until a final match counter has been generated and incremented for each string (e.g., cluster) in the set of strings 175. In some implementations, corresponding counters for each string can also be generated for each hash table 170, to indicate that number of matches in each string of the set of strings 175 to each hash table 170 (e.g., the number of matches on a per-chromosome basis). In such implementations, the total number of matches for a string can be determined by summing the each of the hash table 170 counters for the string.

In some implementations, each string in a set of strings 175 can be a sequence read, and the corresponding set of strings 175 can be a sample file of a genetic sample of a pathogen. In such implementations, the match identifier 140 can iterate through each string, and for each string, generate all possible k-mers utilizing the sliding window techniques described herein (e.g., each k-mer can overlap by the k-mer length minus one bases). For each k-mer extracted from the read, the match identifier 140 can determine (e.g., by performing a lookup) whether the k-mer is present in any of the hash tables 170. If the k-mer is present in one of the hash tables 170, the match identifier 140 can increase a match counter for the read (e.g., the string of the set of strings 175) by one. In some implementations, respective counters can be generated on a per-string basis and on a per-hash table 170 basis (e.g., each string has respective counters for each hash table 170, thereby indicating the number of matches on a per-chromosome basis, for example). In such implementations, the total number of matches for a string can be determined by summing the each of the hash table 170 counters for the string. The match identifier 140 can iterate through each read (e.g., each string of the set of strings 175) until counter values have been generated and updated for each string. The counter values determined using any of the foregoing techniques can be utilized to determine whether a particular string (e.g., a particular read or cluster) satisfies a match threshold, as described in further detail herein.

Once counters for each string of a set of strings 175 have been generated, the subset generator 145 can generate a subset of the set of strings 175 by removing strings with counters that satisfy a predetermined threshold. As described herein, the match identifier 140 can calculate counters for each string, which indicate the total number of matches to the hash tables 170. To identify which strings (e.g., a read or a cluster) should be removed, the subset generator 145 can iterate through each string and compare the total counter value of the string to a predetermined match threshold. The predetermined match threshold can be any number ranging from two to ten matches, for example. However, other predetermined match thresholds are possible, and may be configured by an operator of the data processing system 105 via user input. If a string in the set of strings 175 is associated with a total counter value that is equal to or greater than the predetermined match threshold, the subset generator 145 can mark (e.g., set a flag) the string as corresponding to the hash tables 170 (e.g., corresponding to the human genome, etc.). The subset generator 145 can then generate a subset of the set of strings 175 that includes each of the strings that are not marked, for example, by copying the unmarked strings into a data structure or data package. In some implementations, the subset generator 145 can store an association between each marked string and a corresponding hash table 170 (e.g., chromosome) to which the string matched most frequently (e.g., greatest number of matches). The association can be stored in one or more data structures, and may include an identifier of the hash table 170 (or the chromosome to which the hash table 170 corresponds).

Once the subset generator 145 has generated the subset of the set of strings 175, the subset communicator 150 can transmit the subset to the remote computing system 160. For example, the subset communicator 150 can transmit a data package that includes each of the unmarked strings to the remote computing system 160 via the network 110. The data package may include additional metadata that includes information about the data package or the strings therein (e.g., information about read counts, etc.). In some implementations, the subset communicator 150 can compress the data package using a suitable compression algorithm prior to transmission, to reduce the utilization of network resources. The subset communicator 150 can transmit the data package to the remote computing system 160 in response to a request, or in response to an operator of the data processing system 105 providing user input.

Figure 2:
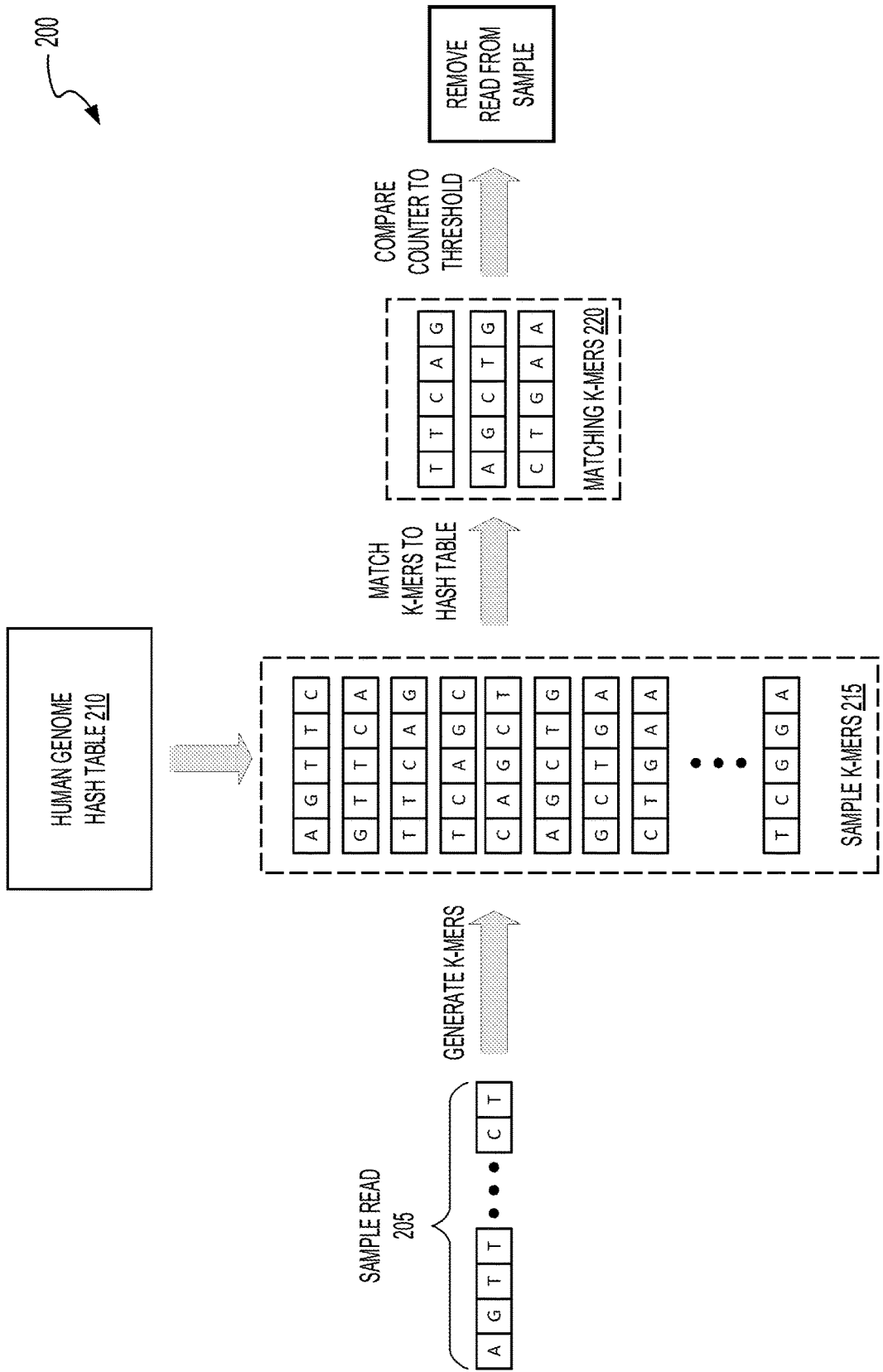
FIG. 2 illustrates an example dataflow diagram of a process for removing string data based on its determined presence in a human genome, in accordance with one or more implementations.

Referring to FIG. 2, illustrated is an example dataflow diagram 200 of a process for removing string data based on its determined presence in a human genome, in accordance with one or more implementations. The process shown in the diagram 200 can be performed, for example, by the data processing system 105 described in connection with FIG. 2. As shown, a sample read 205 (e.g., a read or cluster of a genetic sample of a pathogen) can be matched to one or more human genome hash tables 210 (e.g., one or more hash tables 170).

To do so, the sample k-mers 215 can be generated by iteratively a sliding window of base pairs from the sample read 205. The window can have a number of characters equal to a predetermined length k, with a stride of one character (e.g., one base), such that the sample k-mers 215 overlap by the k-mer size minus one base, as shown. Upon generation, each of the sample k-mers can be matched to the human each human genome hash table 210 (e.g., the hash tables 170) by performing a lookup in the human genome hash table using each sample k-mer 215 to identify the matching k-mers 220. The matching k-mers 220 can be marked as matching to the human genome, as described herein. The data processing system can count the number of matching k-mers 220 extracted from the sample read 205 to determine whether the count satisfies a threshold If the number of matching k-mers 220 satisfies the threshold, the sample read 205 can be removed from the sample prior to transmission to a computing system (e.g., the remote computing system 160).

Although the foregoing description has provided an example use-case for the techniques described herein as applying to genetic data, it should be understood that any type of electronic data may be subjected to the present techniques in order to prevent the transmission of information belonging to a protected corpus. For example, any type of data, such as string data, binary data, hexadecimal data, or network packet data, can be utilized instead of genetic data to achieve desired results. The techniques described herein can be used to efficiently identify and remove any information that matches to the protected corpus, thereby improving both network security and reducing the amount of computational resources required to protect secure data from being transmitted outside of a local network.

Figure 3:
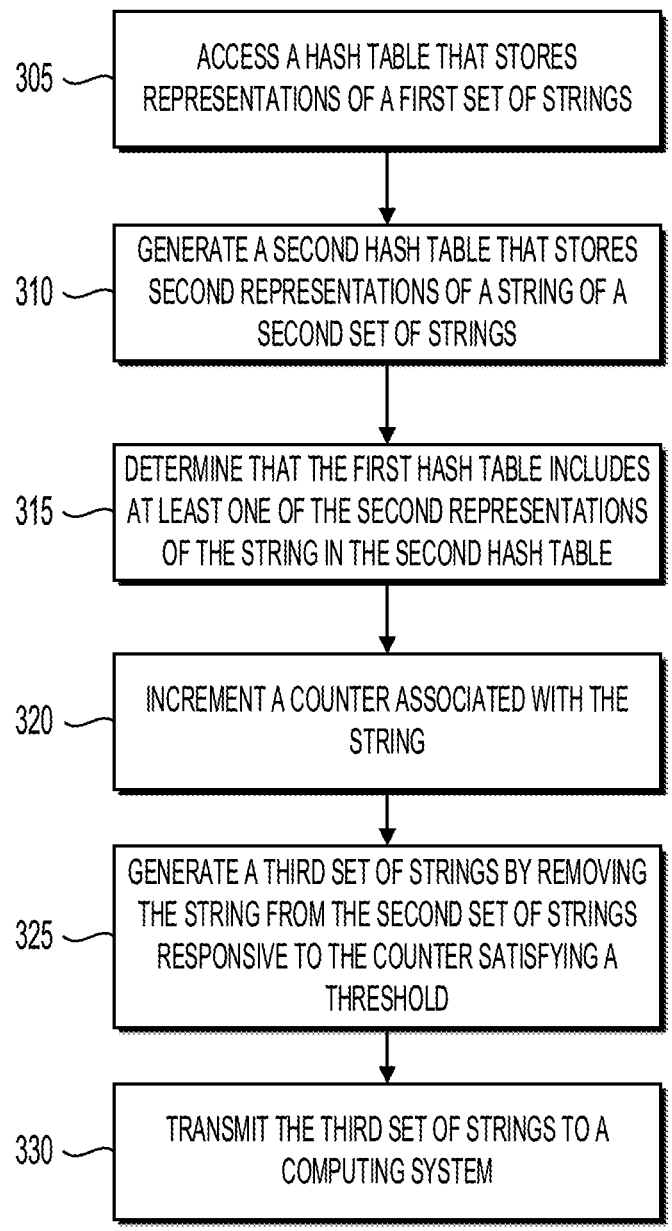
FIG. 3 illustrates a flow chart of an example method for removing data from strings, in accordance with one or more implementations.

FIG. 3 illustrates a flow chart of an example method 300 for removing data from strings, in accordance with one or more implementations. The method 300 can be performed, for example, by a data processing system (e.g., the data processing system 105), or any computing devices described herein (e.g., the computer system 500 of FIG. 5). It should be understood that the method 300 shown in FIG. 3 is an example, and that additional steps may be performed, steps may be omitted, or steps may be performed in a different order than shown, to achieve desired results.

At act 305, the method 300 includes accessing a hash table (e.g., a hash table 170) that stores representations of a first set of strings (e.g., portions of the human genome). The first set of strings can be, for example, reads from a human genome. As described herein, each hash table can correspond to a respective chromosome of the human genome. The hash table can represent each unique k-mer that of a predetermined length (k) that appears in the respective chromosome. The data processing system can access each hash table iteratively, for example, to match the contents of the hash table to corresponding k-mers generated from one or more reads of a pathogenic sample, as described herein. For example, the data processing system can be utilized to access a hash table for a respective chromosome per iteration, until all hash tables have been accessed and matched to the k-mers of the sample.

In some implementations, the data processing system can generate the hash table(s) corresponding to the human genome, for example, in a processing step that occurs prior to pathogenic sample matching. To do so, the data processing system can extract k-mers from a file that includes base pairs of one or more chromosomes of the human genome. The files used to represent the genetic information as described herein can be formed in a text-based format (or a text-based format compressed using a suitable compression algorithm) for representing nucleotide sequences or amino acid (e.g., protein) sequences, in which nucleotides or amino acids are represented using single-letter codes. In a FASTA file format, sequence names and comments can precede the sequences.

If a hash table does not exist for the particular chromosome, the data processing system can generate an empty hash table for the chromosome (e.g., store in storage of the data processing system (e.g., the storage 115) in association with a respective chromosome identifier, etc.). The data processing system can parse the human genome file (e.g., which may be provided by or retrieved from another computing system) to generate a respective hash file for each chromosome in the human genome. As described herein, the data processing system can utilize a predetermined k-mer length (k) when generating the hash tables, which may be provided via user input or retrieved from a local configuration file. The predetermined length may be, for example, fifteen characters, thirty characters, or another suitable length. Once generated, the hash tables can be stored in the storage in association with a respective identifier of the chromosome to which they correspond along with an identifier of the predetermined length k. The hash tables can include only unique k-mers for their corresponding chromosome. The generated hash tables can be utilized by the data processing system or the other components of the data processing system 105 to perform the various functionalities described herein.

At act 310, the method 300 includes generating a second hash table (e.g., a string hash table 180) that stores representations of a string of a second set of strings (e.g., the set of strings 175). As described herein, the string can include genetic information from a cluster of a genetic sample of a pathogen. A cluster can be a genetic building block that makes up the genome of the pathogen, and can include a series of sequential base pairs. Using techniques similar to those described in connection with the hash tables, the data processing system can generate respective empty string hash tables for each cluster. The clusters may be generated, for example, by a pre-processor executed by the data processing system over genetic information from a sample of genetic data from a pathogen, or provided or retrieved from another computing system. A cluster, for example, can correspond to a string in a set of strings. In an embodiment, the string can correspond to a most abundant read in a cluster.

For each string in a set of strings that is not indicated as corresponding to the human genome, the data processing system can iterate through the string base-by-base, shifting one base at a time, to generate overlapping k-mers. The k-mers can be extracted, for example, by iteratively extracting characters from the string using a "sliding window" having a number of characters equal to the predetermined length k, with a stride of one character (e.g., one base). In some implementations, the stride may be greater than one base (e.g., two bases, three bases, any range of bases up to and including the predetermined length, greater than the predetermined length, etc.). The overlapping k-mers can overlap by the k-mer size minus one base. Upon generation, the data processing system can add the extracted k-mer to the string hash table corresponding to the respective string. Each string hash table generated respectively for each string of a set of strings of a genetic sample of a pathogen can be utilized to determine which clusters (e.g., strings) to remove from the sample prior to transmission.

At act 315, the method 300 includes determining that the first hash table includes at least one of the representations of a string of a set of strings (e.g., the set of strings 175) in the second hash table (e.g., corresponding string hash tables). One approach to doing so involves scanning through each first hash table (e.g., each hash table 170) to determine if any k-mers in the first hash table match to a respective k-mer in the second hash files (e.g., the string hash tables corresponding to clusters of a sample). As part of an iterative process, the data processing system can loop through each hash table (e.g., each chromosome of the human genome) by iteratively selecting one hash table. In an iteration, the data processing system can select one of a hash table to match to the string hash tables for a sample. The data processing system can iterate through each string segment (e.g., k-mer) in the selected hash table, and determine whether the respective string segment is present in any of the string hash tables (e.g., corresponding to a pathogenic sample). For example, the data processing system can iteratively select each string hash table, each of which correspond to a respective string (e.g., a respective cluster of a genetic sample of a pathogen), and determine whether any of the string segments (e.g., k-mers) in the selected hash table are present in the selected string hash table.

At act 320, the method 300 can include incrementing a counter associated with a string of the set of strings. If the data processing system determines that a string segment in the selected hash table is present in the selected string hash table (e.g., by performing a lookup, etc.), the data processing system can increment a counter corresponding to the string (e.g., cluster) to which the string hash table corresponds. The counter can indicate, for example, the number of matching k-mers in the cluster that are present in the human genome. The data processing system can repeat this process for each string hash table associated with a set of strings (e.g., for a particular genetic sample), and for each hash table, until a final match counter has been generated and incremented for each string (e.g., cluster) in the set of strings. In some implementations, corresponding counters for each string can also be generated for each hash table, to indicate that number of matches in each string of the set of strings to each hash table (e.g., the number of matches on a per-chromosome basis). In such implementations, the total number of matches for a string can be determined by summing the each of the hash table counters for the string.

At act 325, the method 300 includes generating a third set of strings (e.g., a subset of the set of strings 175) by removing a string from the set of strings responsive to the counter associated with the string satisfying a threshold. As described herein, the data processing system can calculate counters for each string, which indicate the total number of matches to the hash tables. To identify which strings (e.g., a read or a cluster) should be removed, the data processing system can iterate through each string and compare the total counter value of the string to a predetermined match threshold. The predetermined match threshold can be any number ranging from two to ten matches, for example. However, other predetermined match thresholds are possible, and may be configured by an operator of the data processing system via user input. If a string in the set of strings is associated with a total counter value that is equal to or greater than the predetermined match threshold, the data processing system can mark (e.g., set a flag) the string as corresponding to the hash tables (e.g., corresponding to the human genome, etc.). The data processing system can then generate a subset of the set of strings that includes each of the strings that are not marked, for example, by copying the unmarked strings into a data structure or data package. In some implementations, the data processing system can store an association between each marked string and a corresponding hash table (e.g., chromosome) to which the string matched most frequently (e.g., greatest number of matches). The association can be stored in one or more data structures, and may include an identifier of the hash table (or the chromosome to which the hash table corresponds).

At act 330, the method 300 includes transmitting the third set of strings (e.g., the subset of the set of strings 175 that do not satisfy the threshold) to a remote computing system (e.g., the remote computing system 160). For example, the data processing system can transmit a data package that includes each of the unmarked strings to the remote computing system via a network (e.g., the network 110). The data package may include additional metadata that includes information about the data package or the strings therein (e.g., information about read counts, etc.). In some implementations, the data processing system can compress the data package using a suitable compression algorithm prior to transmission, to reduce the utilization of network resources. The data processing system can transmit the data package to the remote computing system in response to a request, or in response to an operator of the data processing system providing user input.

Figure 4:
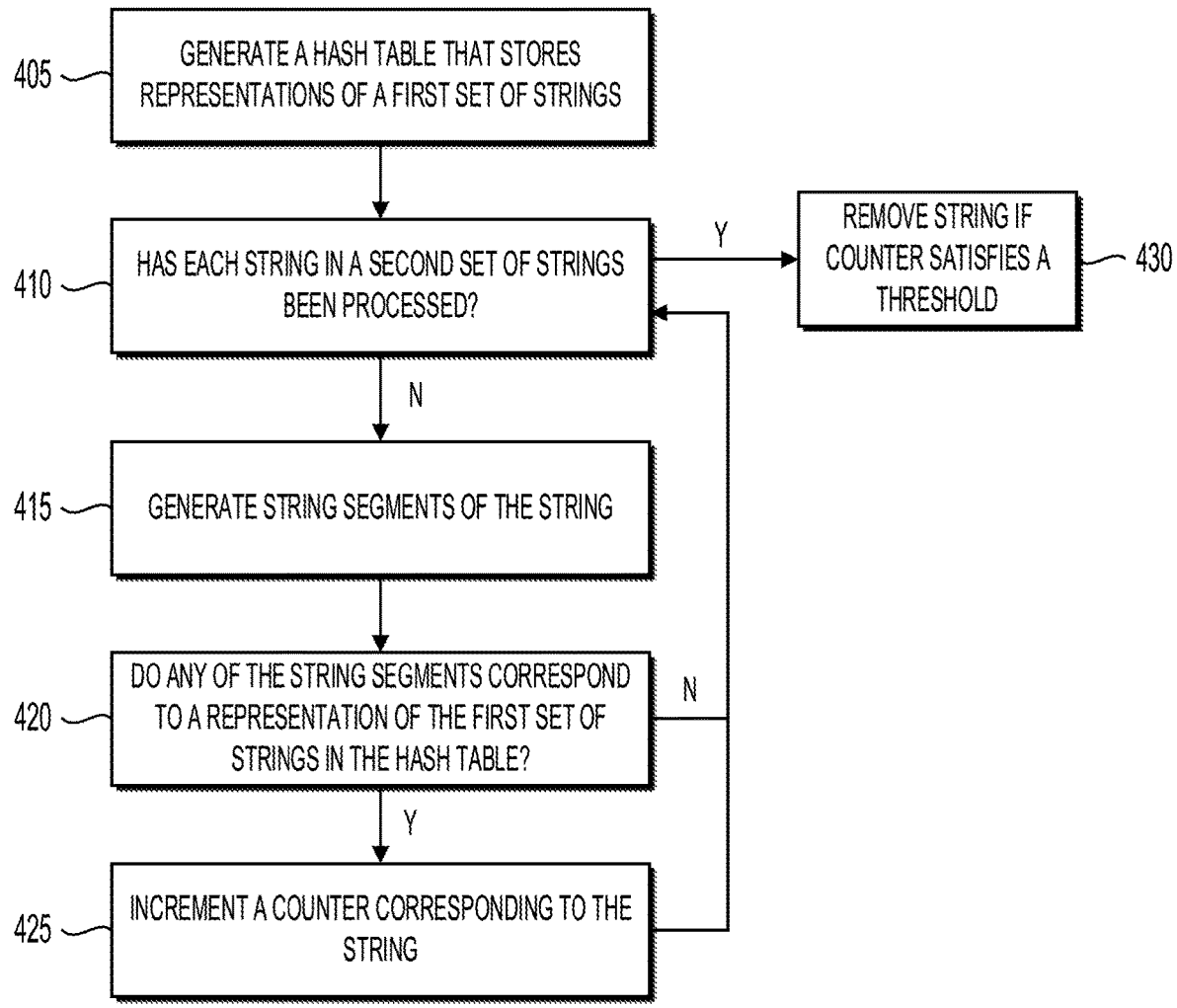
FIG. 4 illustrates a flow chart of another example method for removing data from strings, in accordance with one or more implementations.

FIG. 4 illustrates a flow chart of another example method 400 for removing data from strings, in accordance with one or more implementations. The method 400 can be performed, for example, by a data processing system (e.g., the data processing system 105), or any computing devices described herein (e.g., the computer system 500 of FIG. 5). It should be understood that the method 400 shown in FIG. 4 is an example, and that additional steps may be performed, steps may be omitted, or steps may be performed in a different order than shown, to achieve desired results.

At act 405, the method 400 includes generating one or more hash tables (e.g., one or more hash tables 170) that stores representations of a first set of strings (e.g., genetic data of the human genome). To do so, the data processing system can extract k-mers from a file that includes base pairs of one or more chromosomes of the human genome. The files used to represent the genetic information as described herein can be formed in a text-based format (or a text-based format compressed using a suitable compression algorithm) for representing nucleotide sequences or amino acid (e.g., protein) sequences, in which nucleotides or amino acids are represented using single-letter codes. In a FASTA file format, sequence names and comments can precede the sequences.

If a hash table does not exist for the particular chromosome, the data processing system can generate an empty hash table for the chromosome (e.g., store in storage of the data processing system (e.g., the storage 115) in association with a respective chromosome identifier, etc.). The data processing system can parse the human genome file (e.g., which may be provided by or retrieved from another computing system) to generate a respective hash file for each chromosome in the human genome. As described herein, the data processing system can utilize a predetermined k-mer length (k) when generating the hash tables, which may be provided via user input or retrieved from a local configuration file. The predetermined length may be, for example, fifteen characters, thirty characters, or another suitable length. Once generated, the hash tables can be stored in the storage in association with a respective identifier of the chromosome to which they correspond along with an identifier of the predetermined length k. The hash tables can include only unique k-mers for their corresponding chromosome. The generated hash tables can be utilized by the data processing system or the other components of the data processing system 105 to perform the various functionalities described herein.

At step 410, the method 400 includes determining whether each string in a second set of strings (e.g., a set of strings 175 corresponding to reads from a sample of genetic information from a pathogen) has been processed. As described herein, the data processing system can iteratively process each of the strings (e.g., reads) in a set of strings to determine whether each string matches to the human genome. In some implementations, the data processing system can process each string (e.g., perform acts 415, 420, and 425) sequentially for each string (e.g., one string in the set of strings after another), or in parallel (e.g., each string concurrently, or in concurrent batches, etc.). If each string has been processed using the techniques described herein, the data processing system can perform act 430 of the method 400. If each string has not yet been processed (e.g., acts 415 and 420 have not yet been performed for the string), the data processing system can select the unprocessed string (e.g., a read that is not designated as matching or not matching the human genome) for execution of acts 415 and 420.

At act 415, the method 400 includes generating one or more string segments (e.g., one or more k-mers of the string). To do so, the data processing system can generate all possible k-mers utilizing the sliding window techniques described herein (e.g., each k-mer can overlap by the k-mer length minus one bases). The extracted k-mers can be stored, for example, in a second hash table for the read (e.g., a corresponding string hash table 180), or may be matched directly (e.g., via a lookup) to the hash tables corresponding to the human genome generated in act 405.

At act 420, the method 400 includes determining whether each string segment generated in act 415 corresponds to a representation of the first set of strings (e.g., portions of the human genome) in the hash table generated in act 405. To do so, the data processing system can iterate through each string segment generated in act 415, and perform a lookup in each hash table generated in act 405 (e.g., each human genome hash table, each hash table 170, etc.). If the lookup indicates that the string segment is present in the in the hash tables generated in act 405, the data processing system can proceed to execute 425 using the selected string. Otherwise, the data processing system can execute step 410 to select the next string in the set of strings, if any.

At act 425, the method 400 includes incrementing a counter corresponding to the string selected in act 410. As described herein, if a string segment (e.g., a k-mer) is present in one of the hash tables generated in act 405, the data processing system can increase a match counter for the string by one. The counter can be incremented for each string segment that matches to a hash table in act 420. In some implementations, respective counters can be generated on a per-string basis and on a per-hash table basis (e.g., each string has respective counters for each hash table generated in act 405, thereby indicating the number of matches on a per-chromosome basis, for example). In such implementations, the total number of matches for the string can be determined by summing the each of the hash table counters for the string. The counter values determined using any of the foregoing techniques can be utilized to determine whether a particular string (e.g., a particular read or cluster) satisfies a match threshold, as described in further detail herein.

At act 430, the method 400 includes removing each string having a respective counter that satisfies a threshold. To identify which strings (e.g., a read or a cluster) should be removed, the data processing system can iterate through each string and compare the total counter value of the string to a predetermined match threshold. The predetermined match threshold can be any number ranging from two to ten matches, for example. However, other predetermined match thresholds are possible, and may be configured by an operator of the data processing system via user input. If a string in the set of strings is associated with a total counter value that is equal to or greater than the predetermined match threshold, the data processing system can mark (e.g., set a flag) the string as corresponding to the hash tables (e.g., corresponding to the human genome, etc.). The data processing system can then generate a subset of the set of strings that includes each of the strings that are not marked, for example, by copying the unmarked strings into a data structure or data package. In some implementations, the strings that are marked can be deleted from the set of strings.

Figure 5:
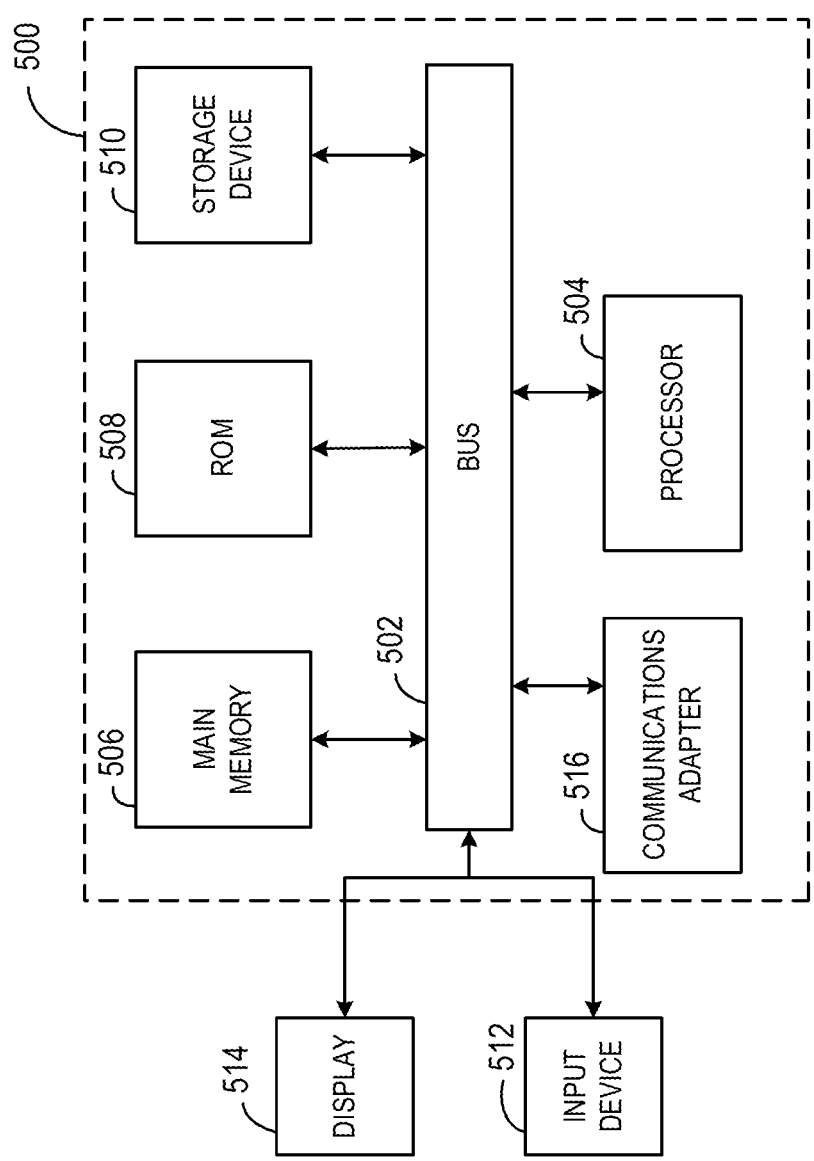
FIG. 5 illustrates a block diagram of an example computing system suitable for use in the various arrangements described herein, in accordance with one or more implementations.

FIG. 5 is a component diagram of an example computing system suitable for use in the various implementations described herein, according to an example implementation. For example, the computing system 500 may implement the data processing system 105 or the remote computing system 160 of FIG. 1, or various other example systems and devices described in the present disclosure.

The computing system 500 includes a bus 502 or other communication component for communicating information and a processor 504 coupled to the bus 502 for processing information. The computing system 500 also includes main memory 506, such as a RAM or other dynamic storage device, coupled to the bus 502 for storing information, and instructions to be executed by the processor 504. Main memory 506 can also be used for storing position information, temporary variables, or other intermediate information during execution of instructions by the processor 504. The computing system 500 may further include a ROM 508 or other static storage device coupled to the bus 502 for storing static information and instructions for the processor 504. A storage device 510, such as a solid-state device, magnetic disk, or optical disk, is coupled to the bus 502 for persistently storing information and instructions.

The computing system 500 may be coupled via the bus 502 to a display 514, such as a liquid crystal display, or active matrix display, for displaying information to a user. An input device 512, such as a keyboard including alphanumeric and other keys, may be coupled to the bus 502 for communicating information, and command selections to the processor 504. In another implementation, the input device 512 has a touch screen display. The input device 512 can include any type of biometric sensor, or a cursor control, such as a mouse, a trackball, or cursor direction keys, for communicating direction information and command selections to the processor 504 and for controlling cursor movement on the display 514.

In some implementations, the computing system 500 may include a communications adapter 516, such as a networking adapter. Communications adapter 516 may be coupled to bus 502 and may be configured to enable communications with a computing or communications network or other computing systems. In various illustrative implementations, any type of networking configuration may be achieved using communications adapter 516, such as wired (e.g., via Ethernet), wireless (e.g., via Wi-Fi, Bluetooth), satellite (e.g., via GPS) pre-configured, ad-hoc, LAN, WAN, and the like.

According to various implementations, the processes of the illustrative implementations that are described herein can be achieved by the computing system 500 in response to the processor 504 executing an implementation of instructions contained in main memory 506. Such instructions can be read into main memory 506 from another computer-readable medium, such as the storage device 510. Execution of the implementation of instructions contained in main memory 506 causes the computing system 500 to perform the illustrative processes described herein. One or more processors in a multi-processing implementation may also be employed to execute the instructions contained in main memory 506. In alternative implementations, hard-wired circuitry may be used in place of or in combination with software instructions to implement illustrative implementations. Thus, implementations are not limited to any specific combination of hardware circuitry and software.

The implementations described herein have been described with reference to drawings. The drawings illustrate certain details of specific implementations that implement the systems, methods, and programs described herein. However, describing the implementations with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As used herein, the term "circuit" may include hardware structured to execute the functions described herein. In some implementations, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some implementations, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexers, registers, capacitors, inductors, diodes, wiring, and so on.

The "circuit" may also include one or more processors communicatively coupled to one or more memory or memory devices. In this regard, the one or more processors may execute instructions stored in the memory or may execute instructions otherwise accessible to the one or more processors. In some implementations, the one or more processors may be embodied in various ways. The one or more processors may be constructed in a manner sufficient to perform at least the operations described herein. In some implementations, the one or more processors may be shared by multiple circuits (e.g., circuit A and circuit B may comprise or otherwise share the same processor, which, in some example implementations, may execute instructions stored, or otherwise accessed, via different areas of memory). Alternatively or additionally, the one or more processors may be structured to perform or otherwise execute certain operations independent of one or more co-processors.

In other example implementations, two or more processors may be coupled via a bus to enable independent, parallel, pipelined, or multi-threaded instruction execution. Each processor may be implemented as one or more general-purpose processors, ASICs, FPGAs, GPUs, TPUs, digital signal processors (DSPs), or other suitable electronic data processing components structured to execute instructions provided by memory. The one or more processors may take the form of a single core processor, multi-core processor (e.g., a dual core processor, triple core processor, or quad core processor), microprocessor, etc. In some implementations, the one or more processors may be external to the apparatus, for example, the one or more processors may be a remote processor (e.g., a cloud-based processor). Alternatively or additionally, the one or more processors may be internal or local to the apparatus. In this regard, a given circuit or components thereof may be disposed locally (e.g., as part of a local server, a local computing system) or remotely (e.g., as part of a remote server such as a cloud based server). To that end, a "circuit" as described herein may include components that are distributed across one or more locations.

An exemplary system for implementing the overall system or portions of the implementations might include a general purpose computing devices in the form of computers, including a processing unit, a system memory, and a system bus that couples various system components including the system memory to the processing unit. Each memory device may include non-transient volatile storage media, non-volatile storage media, non-transitory storage media (e.g., one or more volatile or non-volatile memories), etc. In some implementations, the non-volatile media may take the form of ROM, flash memory (e.g., flash memory such as NAND, 3D NAND, NOR, 3D NOR), EEPROM, MRAM, magnetic storage, hard discs, optical discs, etc. In other implementations, the volatile storage media may take the form of RAM, TRAM, ZRAM, etc. Combinations of the above are also included within the scope of machine-readable media. In this regard, machine-executable instructions comprise, for example, instructions and data, which cause a general-purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components), in accordance with the example implementations described herein.

It should also be noted that the term "input devices," as described herein, may include any type of input device including, but not limited to, a keyboard, a keypad, a mouse, joystick, or other input devices performing a similar function. Comparatively, the term "output device," as described herein, may include any type of output device including, but not limited to, a computer monitor, printer, facsimile machine, or other output devices performing a similar function.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative implementations. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

While this specification contains many specific implementation details, these should not be construed as limitations on the scope of any inventions or of what may be claimed, but rather as descriptions of features specific to particular implementations of the systems and methods described herein. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub combination.

In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Having now described some illustrative implementations and implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed only in connection with one implementation are not intended to be excluded from a similar role in other implementations.

The phraseology and terminology used herein is for the purpose of description and should not be regarded as limiting. The use of "including," "comprising," "having," "containing," "involving," "characterized by," "characterized in that," and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act, or element may include implementations where the act or element is based at least in part on any information, act, or element.

Any implementation disclosed herein may be combined with any other implementation, and references to "an implementation," "some implementations," "an alternate implementation," "various implementation," "one implementation," or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

The foregoing description of implementations has been presented for purposes of illustration and description. It is not intended to be exhaustive or to limit the disclosure to the precise form disclosed, and modifications and variations are possible in light of the above teachings or may be acquired from this disclosure. The implementations were chosen and described in order to explain the principals of the disclosure and its practical application to enable one skilled in the art to utilize the various implementations and with various modifications as are suited to the particular use contemplated. Other substitutions, modifications, changes, and omissions may be made in the design, operating conditions and implementation of the implementations without departing from the scope of the present disclosure as expressed in the appended claims.

What is claimed is:

1. A system, comprising:
   one or more processors coupled to memory, the one or more processors configured to:
   access a hash table that stores a plurality of first k-mers of a human genome, each first k-mer of the plurality of first k-mers corresponding to a first number of characters (k);
   generate a plurality of second k-mers of a read of a cluster of a plurality of clusters, the plurality of clusters obtained from a sample;
   determine a second number of the plurality of second k-mers that match at least one of the plurality of first k-mers in the hash table;
   generate a subset of the plurality of clusters by removing the cluster from the plurality of clusters responsive to the second number satisfying a threshold; and
   transmit the subset of the plurality of clusters to a computing system.

2. The system of claim 1, wherein the one or more processors are further configured to generate the hash table that stores the plurality of first k-mers of the human genome, each of the plurality of first k-mers corresponding to non-overlapping portions of the human genome.

3. The system of claim 1, wherein the one or more processors are further configured to generate the plurality of second k-mers based on each base in the read.

4. The system of claim 1, wherein the one or more processors are further configured to generate a second hash table based on the plurality of second k-mers.

5. The system of claim 4, wherein the one or more processors are further configured to determine the second number based on the hash table and the second hash table.

6. The system of claim 4, wherein each of the plurality of first k-mers have a length of one of at least fifteen, at least thirty, at least forty-five, or at least fifty.

7. The system of claim 1, wherein the one or more processors are further configured to determine the second number by performing a lookup in the hash table using each of the plurality of second k-mers.

8. The system of claim 1, wherein the one or more processors are further configured to store an association between the cluster and an identifier of a chromosome to which the plurality of first k-mers correspond.

9. The system of claim 1, wherein the one or more processors are further configured to extract the plurality of first k-mers from one or more of FASTA format file, a FASTQ format file, a FASTQ.GZ format file, an FNA format file, or a BAM format file of the human genome.

10. The system of claim 1, wherein the plurality of first k-mers correspond to a first chromosome file of the human genome.

11. A system, comprising:
one or more processors coupled to memory, the one or more processors configured to:
  access a first hash table that stores a plurality of first k-mers of a human genome, each k-mer of the plurality of first k-mers corresponding to a predetermined number of characters (k);
  generate a second hash table that stores the plurality of second k-mers of a read of a cluster of plurality of clusters obtained from a sample of a pathogen, each second k-mer of the plurality of second k-mers corresponding to the predetermined number of characters (k);
  responsive to determining, based on the first hash table and the second hash table, that the first hash table includes at least one of the plurality of second k-mers of the read included in the second hash table, increment a counter associated with the cluster;
  generate a subset of the plurality of clusters by removing the cluster from the plurality of clusters responsive to determining that the counter satisfies a threshold; and
  transmit the subset of the plurality of clusters to a computing system.

12. The system of claim 11, wherein the one or more processors are further configured to generate the first hash table that stores the plurality of first k-mers of the human genome, each of the plurality of first k-mers corresponding to non-overlapping portions of the human genome.

13. The system of claim 11, wherein the one or more processors are further configured to generate the plurality of second k-mers based on each base in the read.

14. The system of claim 11, wherein the one or more processors are further configured to present an indication of a chromosome in the human genome to which the cluster corresponds.

15. A system, comprising:
one or more processors coupled to memory, the one or more processors configured to:
  generate a hash table that stores a plurality of representations of a first set of strings, each representation of the plurality of representations corresponding to a predetermined number of characters;
  for each string in a second set of strings:
    generate a string segment of the string having the predetermined number of characters; and
    responsive to determining that the string segment corresponds to at least one of the plurality of representations of the first set of strings in the hash table, increment a counter associated with the second set of strings; and
  remove the string from a plurality of strings responsive to the counter satisfying a threshold.

16. The system of claim 15, wherein the first set of strings corresponds to genetic data of a human genome.

17. The system of claim 15, wherein the string segment comprises a k-mer, and wherein the one or more processors are further configured to determine that the string segment corresponds to at least one of the plurality of representations in the hash table by performing a lookup in the hash table using the k-mer.

18. A system, comprising:
one or more processors coupled to memory, the one or more processors configured to:
  access a first hash table that stores a plurality of representations of a first set of strings, each representation of the plurality of representations corresponding to a predetermined number of characters;
  generate a second hash table that stores a plurality of second representations of a string of a second set of strings, each second representation of the plurality of second representations corresponding to the predetermined number of characters;
  responsive to determining, based on the first hash table and the second hash table, that the first hash table includes at least one of the plurality of second representations of the string included in the second hash table, increment a counter associated with the second set of strings;
  generate a third set of strings by removing the string from the second set of strings responsive to determining that the counter satisfies a threshold; and
  transmit the third set of strings to a computing system.

19. The system of claim 18, wherein the one or more processors are further configured to pre-process a sequence file to generate the first set of strings.

20. The system of claim 18, wherein the second hash table corresponds to a cluster of genetic information obtained from a sample.

* * * * *